United States Patent [19]

Sugiura et al.

[11] Patent Number: 5,110,827

[45] Date of Patent: May 5, 1992

[54] IMIDAZOLE COMPOUNDS HAVING FUNGICIDAL ACTIVITY

[76] Inventors: Hisao Sugiura; Takashi Nishimura; Toshinobu Tanaka, all of c/o Ube Research Laboratory, Ube Industries, Ltd., 1978-5, Oaza Kogushi, Ube-shi, Yamaguchi-ken, Japan

[21] Appl. No.: 603,996

[22] Filed: Oct. 26, 1990

[30] Foreign Application Priority Data

Nov. 21, 1989 [JP] Japan ................. 1-300858
Nov. 21, 1989 [JP] Japan ................. 1-300859

[51] Int. Cl.$^5$ .............. A01N 43/50; C00D 233/60
[52] U.S. Cl. ........................... 514/399; 548/341
[58] Field of Search ................. 548/341; 514/399

[56] References Cited

U.S. PATENT DOCUMENTS 4,500,536  2/1985  Yoshida et al. ............... 514/397
4,902,705  2/1990  Hirota et al. ................. 514/397

FOREIGN PATENT DOCUMENTS 58-150590  9/1983  Japan .
60-260572  12/1985  Japan .

OTHER PUBLICATIONS

Ehler, "Reactions of Carbamylimidazoles with, etc.", CA85: 108961h (1976), RN #59643-40-2.

Primary Examiner—Patricia L. Morris

[57] ABSTRACT

There are disclosed an imidazole derivative represented by the formula:

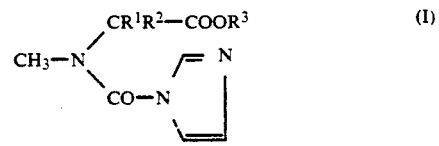

wherein $R^1$ and $R^2$ each represent a hydrogen atom or a $C_{1-4}$ alkyl group, provided that both of $R^1$ and $R^2$ do not represent an alkyl group at the same time, or may be combined with each other to form a group $=CHR^4$, where $R^4$ represents a $C_{1-4}$ alkyl group; when $R^1$ and $R^2$ each represent a hydrogen atom or a $C_{1-4}$ alkyl group, $R^3$ represents a $C_{1-12}$ alkyl group, a $C_{1-12}$ alkenyl group, a phenylalkyl group, a phenylalkenyl group, a phenoxyalkyl group or a phenoxyalkenyl group; and when $R^1$ and $R^2$ represent a group $=CHR^4$, $R^3$ represents a $C_{4-10}$ alkyl group, a $C_{4-10}$ alkenyl group or a phenylalkyl group;

a method for preparing the same and a fungicide containing the same as an active ingredient and a fungicidally acceptable carrier.

10 Claims, No Drawings

IMIDAZOLE COMPOUNDS HAVING FUNGICIDAL ACTIVITY

BACKGROUND OF THE INVENTION

This invention relates to an imidazole derivative, a method for preparing the same and a fungicide containing the same as an active ingredient.

As imidazole derivatives, for example, there have been known compounds disclosed in (1) Japanese Provisional Patent Publication No. 150590/1983 and (2) Japanese Provisional Patent Publication No. 260572/1985.

However, in (1), it is disclosed that the imidazole derivative of the formula:

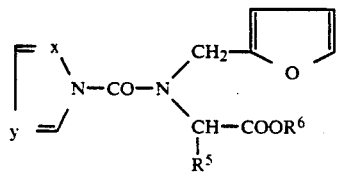

(wherein $R^5$ represents a hydrogen atom, a methyl group or an ethyl group; $R^6$ represents a lower alkyl group; and x and y each represent a carbon atom or a nitrogen atom) has fungicidal activity, but these compounds have too complicated structures to be prepared on an industrial scale, and can be hardly said to have sufficient efficacy.

In (2), it is disclosed that the imidazole derivatives of the formula:

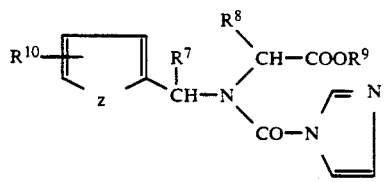

(wherein $R^7$ represents a hydrogen atom or a lower alkyl group; $R^8$ represents a lower alkyl group; $R^9$ represents an alkenyl group, a cycloalkyl group, an alkocyalkyl group or a higher alkyl group; $R^{10}$ represents a hydrogen atom or a lower alkyl group; z represents an oxygen atom or a sulfur atom) have fungicidal activity, but these compounds have also too complicated structures to be prepared on an industrial scale, and can hardly be said to have sufficient efficacy.

SUMMARY OF THE INVENTION

An object of the present invention is to provide a novel imidazole derivative, a method for preparing the same and a fungicide comprising the same as an active ingredient.

The present inventors have studied intensively in order to solve the problems as mentioned above, and consequently found that a novel imidazole derivative has a strong fungicidal activity, to accomplish the present invention.

More specifically, the present invention concerns:
(1) a compound of the formula:

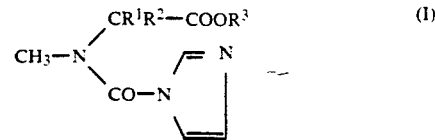

wherein $R^1$ and $R^2$ each represents a hydrogen atom or an alkyl group having 1 to 4 carbon atoms, provided that both of $R^1$ and $R^2$ do not represent an alkyl group at the same time, or may be combined with each other to form a group $=CHR^4$, where $R^4$ represents an alkyl group having 1 to 4 carbon atoms; when $R^1$ and $R^2$ each represents a hydrogen atom or an alkyl group having 1 to 4 carbon atoms, $R^3$ represents an alkyl group having 1 to 12 carbon atoms, an alkenyl group having 1 to 12 carbon atoms, a phenylalkyl group, a phenylalkenyl group, a phenoxyalkyl group or a phenoxyalkenyl group, and these phenyl rings may be substituted with at least one of a halogen atom, an alkyl group, an alkoxy group, an alkenyloxy group and a phenoxy group; and when $R^1$ and $R^2$ represent a group $=CHR^4$, $R^3$ represents an alkyl group having 4 to 10 carbon atoms, an alkenyl group having 4 to 10 carbon atoms or a phenylalkyl group, and these phenyl rings may be substituted;

(2) a method for preparing a compound of the above formula (I), which comprises reacting a compound of the formula:

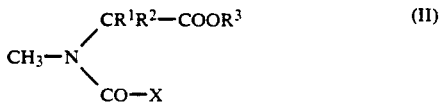

wherein $R^1$, $R^2$ and $R^3$ have the same meanings as defined above; and X represents an eliminatable group, with imidazole; and (3) a fungicide comprising a compound of the above formula (I) as an active ingredient, and a fungicidally acceptable carrier.

DESCRIPTION OF THE PREFERRED EMBODIMENTS

In the novel imidazole derivative (I) which is the desired compound and the compound (II) which is the starting material for preparation thereof, examples of $R^1$ and $R^2$ may include a hydrogen atom and an alkyl group having 1 to 4 carbon atoms (e.g. a methyl group, an ethyl group, a propyl group and a butyl group), preferably a hydrogen atom, a methyl group, an ethyl group or a propyl group, more preferably an ethyl group. However, the case where both of $R^1$ and $R^2$ are simultaneously the alkyl groups is excluded. Also, $R^1$ and $R^2$ may be combined with each other to form a group $=CHR^4$ where $R^4$ represents a hydrogen atom and an alkyl group having 1 to 4 carbon atoms (e.g. a methyl group, an ethyl group, a propyl group and a butyl group), preferably a methyl group.

When $R^1$ and $R^2$ each represent a hydrogen atom or an alkyl group having 1 to 4 carbon atoms, provided that both of $R^1$ and $R^2$ do not represent an alkyl group at the same time, examples of $R^3$ may include an alkyl group having 1 to 12 carbon atoms, an alkenyl group having 1 to 12 carbon atoms, a phenylalkyl group, a phenylalkenyl group, a phenoxyalkyl group and a phenoxyalkenyl group.

As the alkyl group having 1 to 12 carbon atoms as mentioned above, straight and branched ones can be included, preferably straight ones, more preferably a straight alkyl group having 5 to 10 carbon atoms.

As the alkenyl group having 1 to 12 carbon atoms as mentioned above, straight, branched ones can be included, preferably straight ones, more preferably a straight alkenyl group having 4 to 10 carbon atoms, further preferably a straight alkenyl group having 6 carbon atoms.

As the alkyl in the phenylalkyl group as mentioned above, straight or branched ones can be included, preferably straight or branched ones having 1 to 10 carbon atoms, more preferably straight ones having 1 to 5 carbon atoms.

As the alkenyl in the phenylalkenyl group as mentioned above, straight or branched ones having 3 to 12 carbon atoms can be included, preferably straight ones having 3 to 6 carbon atoms, more preferably a straight one having 3 carbon atoms.

As the alkyl in the phenoxyalkyl group as mentioned above, straight or branched ones having 2 to 12 carbon atoms can be included, preferably straight or branched ones having 2 to 5 carbon atoms.

As the alkenyl in the phenoxyalkenyl group as mentioned above, straight or branched ones having 3 to 12 carbon atoms can be included, preferably straight or branched ones having 3 to 5 carbon atoms.

These above-mentioned phenyl rings may be also substituted by at least one substituent selected from the group consisting of a halogen atom, an alkyl group, an alkoxy group, an alkenyloxy group and a substituted or unsubstituted phenoxy group.

When $R^1$ and $R^2$ represent a group $=CHR^4$, $R^3$ represents an alkyl group having 4 to 10 carbon atoms or a phenylalkyl group, and these phenyl rings may be also substituted. Examples of $R^3$ may include a straight or branched alkyl group having 4 to 10 carbon atoms, a straight or branched alkenyl group having 4 to 10 carbon atoms, a phenylalkyl group which may be substituted by a straight or branched, alkyl group having 1 to 12 carbon atoms, preferably a straight or branched alkenyl group having 4 to 10 carbon atoms and a phenylalkyl group substituted by a straight or branched alkyl group having 1 to 12 carbon atoms, more preferably a straight alkenyl group having 4 to 6 carbon atoms and a phenylalkyl group substituted by a straight alkyl group having 1 to 4 carbon atoms. The phenyl ring may be substituted by at least one substituent selected from the group consisting of a halogen atom, an alkyl group, an alkoxy group, an alkenyloxy group and a substituted or unsubstituted phenoxy group.

In the present invention, the following compounds represented by the formulae (I') and (I'') are preferred.

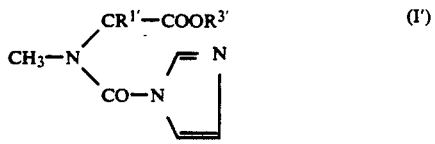

wherein $R^{1'}$ represents an alkyl group having 1 to 4 carbon atoms; and $R^{3'}$ represents an alkyl group having 1 to 12 carbon atoms, an alkenyl group having 1 to 12 carbon atoms, a phenylalkyl group, a phenylalkenyl group, a phenoxyalkyl group or a phenoxyalkenyl group, and these phenyl rings may be also substituted with at least one of a halogen atom, an alkyl group, an alkoxy group, an alkenyloxy group or a phenoxy group;

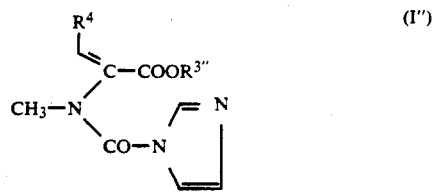

wherein $R^4$ represents an alkyl group having 1 to 4 carbon atoms; and $R^{3''}$ represents an alkyl group having 4 to 10 carbon atoms, an alkenyl group having 4 to 10 carbon atoms or a phenylalkyl group, and these phenyl rings may be also substituted.

X is not particularly limited, but may include, for example, a halogen atom (e.g. a chlorine atom, a bromine atom, an iodine atom), an alkylthio group (e.g. a methylthio group, an ethylthio group, a butylthio group), an alkanesulfonyloxy group which may be substituted with a halogen atom (e.g. a methanesulfonyloxy group, an ethanesulfonyloxy group, a trifluoromethanesulfonyloxy group), an arylsulfonyloxy group (e.g. a benzenesulfonyloxy group, a p-toluenesulfonyloxy group) and a hydroxy group, preferably a halogen atom.

The starting compound (II) to be used in the present invention can be prepared easily by reacting a secondary amine with phosgene.

The desired compound (I) should be generally preferred to be prepared by reacting the starting compound (II) with imidazole in a solvent in the presence of a base, but it can be also obtained by carrying out the reaction without addition of a base, or alternatively it can be also obtained by reacting the starting compound (II) with imidazole by melting under heating in absence of a solvent.

The solvent is not particularly limited, provided that it does not directly participate in the present reaction, as exemplified by aromatic, aliphatic, alicyclic hydrocarbons which are chlorinated or not such as benzene, toluene, xylene, methylnaphthalene, petroleum ether, ligroin, hexane, chlorobenzene, dichlorobenzene, methylene chloride, chloroform, dichloroethane, trichloroethylene, cyclohexane; ethers such as diethyl ether, dimethyl ether, tetrahydrofuran, dioxane; ketones such as acetone, methyl ethyl ketone; alcohols such as methanol, ethanol, ethylene glycol or hydrous mixtures thereof; amides such as N,N-dimethylformamide, N,N-dimethylacetamide; organic bases such as pyridine, N,N-diethylaniline; 1,3-dimethyl-2-imidazolidinone; dimethyl sulfoxide; mixtures of the above-mentioned solvents; and so on.

Examples of the base may include organic bases such as triethylamine, pyridine, N,N-diethylaniline; alkali metal alkoxides such as sodium methoxide, sodium ethoxide; inorganic bases such as sodium amide, sodium hydroxide, potassium hydroxide, potassium carbonate, sodium carbonate and sodium hydride.

In the preparation method, the starting compound (II) and the imidazole employed can be added at a ratio of 0.5 to 5.0 moles of imidazole, but preferably 1.0 to 2.0 mole, to 1 mole of the starting compound (II).

The reaction temperature is not particularly limited, provided that the reaction is carried out at a temperature not higher than the boiling point of the solvent employed, but it is preferred to shorten the reaction time by way of heating, and it may be, for example, 20 to 150° C., preferably 50 to 100° C.

The reaction time may be generally 10 minutes to 8 hours, preferably 1 to 3 hours.

The desired compound (I) can be easily obtained by suitably purifying the reaction product according to known means such as recrystallization and various chromatography.

The desired compound (I) of the present invention exhibits excellent effects for prevention and therapy of crop diseases caused by plant pathogenic fungi such as powdery mildew, rust, eyespot, leaf blight, blast, brown spot, sheath blight, gray mold, Sclerotinia rot, seedling dampingoff, brown rot, black rot, "Bakanae" disease and scab, and also exhibits excellent effects for prevention and therapy of crop diseases caused by resistant microorganisms to existing agricultural chemicals.

The fungicide of the present invention contains at least one kind of the compounds (I) as the active ingredient.

The compound (I) can be also used alone, but for the purpose of saving energy and enhancing the control effect, it can be used as a mixture with other fungicides, herbicides and plant growth controllers. It is generally preferred to use the compound in a formulation together with carrier, surfactant, dispersing agent and auxiliary agent (for example, prepared as a composition of powder, emulsion, fine granules, granules, wettable agent, oily suspension and aerosol).

Examples of the carrier may include solid carriers such as talc, bentonite, clay, kaolin, diatomaceous earth, white carbon, vermiculite, slaked lime, siliceous sand, ammonium sulfate, urea and others; liquid carriers such as hydrocarbons (e.g. kerosene and mineral oils), aromatic hydrocarbons (e.g. benzene, toluene and xylene), chlorinated hydrocarbons (e.g. chloroform and carbon tetrachloride), ethers (e.g. dioxane and tetrahydrofuran), ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethyl sulfoxide), water and others; and gaseous carriers such as air, nitrogen, carbon dioxide, Freon (trade name) and others (in this case, mixed jetting is possible).

Examples of surfactants or dispersing agents which can be used for improving performances of the present agent such as attachment onto animals and plants, improvement of absorption, dispersion, emulsification and spreading of the chemical, can include alcohol sulfuric acid esters, alkylsulfonic acid salts, ligninsulfonic acid salts and polyoxyethylene glycol ethers. For improvement of the properties of the preparations, carboxymethyl cellulose, polyethylene glycol and gum arabic can be used as the auxiliary agent.

In preparation of the present agent, the above-mentioned carriers, surfactants, dispersing agents and auxiliary agents can be used each individually or in a suitable combination.

The active ingredient concentration when the compound (I) of the present invention is formed into a preparation may be generally 1 to 50 % by weight for emulsion, generally 0.3 to 25 % by weight for powder, generally 1 to 90 % by weight for wettable agent, generally 0.5 to 5 % by weight for granules, generally 0.5 to 5 % by weight for oil agent, generally 0.1 to 5 % by weight for aerosol.

By diluting these preparations to appropriate concentrations and spraying onto plant stalk and leaf, soil, water face of paddy field, or applying directly depending on the respective purposes, they can be provided for various uses.

EXAMPLES

In the following, the present invention is described by referring to Reference examples and Examples, but these examples do not limit the scope of the present invention at all.

Reference example 1

Synthesis of
N-1-(1-p-n-butoxybenzyloxycarbonyl)propyl-N-chlorocarbonyl-methylamine Trichloromethylchloroformate (3.0 g, 15 mmole) and triethylamine (4.0 g, 60 mmole) were dissolved in toluene (100 ml), and into the resulting solution was added dropwise at room temperature under stirring N-1-(1-p-n-butoxybenzyloxycarbonyl)propyl-N-methylamine solution (4.7 g/toluene 30 ml). After the mixture was stirred at room temperature for 30 minutes, it was thrown into water, the toluene layer was concentrated and dried to give a slurry of the desired product.

This product was used without purification for subsequent synthesis.

EXAMPLE 1

Synthesis of
N-1-(1-p-n-butoxybenzyloxycarbonyl)propyl-N-(1-imidazolylcarbonyl)-methylamine The unpurified starting compound (II') (3.4 g, 10 mmole) of Reference example 1, imidazole (1.0 g, 15 mmole) and triethylamine (1.5 g, 15 mmole) were dissolved in toluene (30 ml) as a solvent, and the resulting solution was stirred under heating at 55° C. for one hour. After completion of the reaction, the reaction mixture was washed with water, dried over anhydrous sodium sulfate and then toluene was evaporated under reduced pressure.

The residue obtained was isolated by silica gel column chromatography (Wako Gel C-200, eluted with toluene : ethyl acetate=8:1) to give 3.2 g of the desired product as a colorless crystalline solid.

EXAMPLES 2 to 33

According to the same method as in Example 1, the desired compounds (I') shown in Table 1 were obtained.

TABLE 1

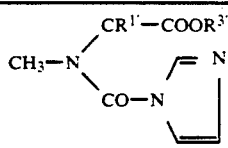 (I')

| Example | R¹' | R³' | Physical property |
|---|---|---|---|
| 1 | $C_2H_5$ | $-CH_2-C_6H_4-O-C_4H_9$ | $n_D^{22}$ 1.5295 |
| 2 | " | $-C_5H_{11}(n)$ | $n_D^{25}$ 1.4846 |
| 3 | " | $-(CH_2)_4CH=CH_2$ | $n_D^{27}$ 1.4986 |
| 4 | " | $-C_6H_{13}(n)$ | $n_D^{27}$ 1.4840 |
| 5 | " | $-C_8H_{17}(n)$ | $n_D^{27}$ 1.4812 |
| 6 | " | $-C_{10}H_{21}(n)$ | $n_D^{27}$ 1.4803 |
| 7 | " | $-C_3H_6-C_6H_5$ | $n_D^{26}$ 1.5298 |
| 8 | " | $-C_4H_8-C_6H_5$ | $n_D^{26}$ 1.5250 |
| 9 | " | $-C_5H_{10}-C_6H_5$ | $n_D^{26}$ 1.5228 |
| 10 | " | $-CH_2-C_6H_4-OCH_3$ | $n_D^{26}$ 1.5378 |
| 11 | " | $-CH_2-C_6H_4-OC_3H_7$ | $n_D^{25}$ 1.5302 |
| 12 | " | $-CH_2-C_6H_4-OC_5H_{11}$ | m.p. 63~65° C. |
| 13 | " | $-CH_2-C_6H_4-OC_6H_{13}$ | m.p. 59~61° C. |
| 14 | " | $-C_2H_4O-C_6H_4-O-C_6H_5$ | m.p. 103~105° C. |
| 15 | " | $-CH_2-C_6H_4-O-C_6H_5$ | $n_D^{25}$ 1.5646 |
| 16 | " | $-C_2H_4O-C_6H_3(Cl)_2$ (3,4-Cl) | $n_D^{23}$ 1.5431 |
| 17 | " | $-C_2H_4O-C_6H_3(Cl)_2$ (2,6-Cl) | $n_D^{23}$ 1.5442 |
| 18 | $C_2H_5$ | $-C_2H_4O-C_6H_4-C_2H_4OC_2H_5$ | $n_D^{23}$ 1.5378 |
| 19 | " | $-CH_2-C_6H_4-Cl$ (2,4-Cl disub.) | m.p. 70~72° C. |
| 20 | H | $-CH_2-C_6H_4-OC_4H_9$ | m.p. 95~97° C. |
| 21 | $C_2H_5$ | $-CH_2-C_6H_3(Cl)_2-OC_4H_9$ | $n_D^{23}$ 1.5334 |
| 22 | " | $-CH_2-C_6F_4-F$ (pentafluoro) | m.p. 89~91° C. |
| 23 | " | $-CH_2-C_6H_4-OC_4H_9$ | $n_D^{25}$ 1.5263 |
| 24 | " | $-CH_2-C_6H_3(Cl)_2-OC_2H_4Br$ | $n_D^{23}$ 1.5562 |
| 25 | " | $-CH_2-C_6H_3(Cl)-OC_4H_9$ | $n_D^{26}$ 1.5312 |
| 26 | " | $-CH_2-C_6H_4-C(CH_3)_3$ | $n_D^{26}$ 1.5254 |
| 27 | " | $-CH_2-C_6H_4-C(CH_3)_2$ | $n_D^{24}$ 1.5312 |
| 28 | $C_3H_7(n)$ | $-CH_2-C_6H_4-OC_4H_9$ | m.p. 64~66° C. |
| 29 | $CH_3$ | $-CH_2-C_6H_4-OC_4H_9$ | m.p. 67~69° C. |
| 30 | $C_2H_5$ | $-CH_2-C_6H_4-OCHCH_3CHCH_2$ | $n_D^{21}$ 1.5390 |
| 31 | " | $-CH_2-C_6H_4-OCHCH_3C_2H_5$ | $n_D^{21}$ 1.5296 |
| 32 | " | $-CH_2CHCH_3-C_6H_4-C_2H_5$ | $n_D^{27}$ 1.5271 |
| 33 | " | $-C_2H_5CHCH-C_6H_5$ | $n_D^{26}$ 1.5368 |

Of these compounds, particularly preferred are Compounds Nos. 1, 4, 5, 11 and 12.

REFERENCE EXAMPLE 2

Synthesis of N-1-(1-p-n-amyloxybenzyloxycarbonyl)propyliden-1-yl-N-chlorocarbonyl-methylamine N-1-(1-p-n-amyloxybenzyloxycarbonyl)propyliden-methylamine (5.8 g, 20 mmole) was dissolved in toluene (100 ml), and into the resulting solution was added trichloromethyl formate (3.0 g, 15 mmole). Subsequently, to the resulting solution was added dropwise at room temperature under stirring triethylamine (4.0 g, 60 mmole). After the mixture was stirred at room temperature for 30 minutes, it was thrown into water, the toluene layer was concentrated and dried to give a slurry of the desired product.

This product was used without purification for subsequent synthesis.

EXAMPLE 34

Synthesis of N-1-(1-p-n-amyloxybenzyloxycarbonyl)propyliden-1-yl-N-(1-imidazolylcarbonyl)-methylamine The unpurified starting compound (II") (3.5 g, 10 mmole) of Reference example 2, imidazole (1.0 g, 15 mmole) and potassium carbonate (2.1 g, 15 mmole) were dissolved in dimethylformamide (30 ml) as a solvent, and the resulting solution was stirred under heating at 45° C. for 2 hours. After completion of the reaction, water was added to the reaction mixture, and then was added toluene to extract the mixture. Then, the extracted toluene layer was washed with water, dried over anhydrous sodium sulfate and then toluene was evaporated under reduced pressure.

The residue obtained was isolated by silica gel column chromatography (Wako Gel C-200, eluted with toluene : ethyl acetate=8:1) to give 3.0 g of the desired product as a pale yellow crystalline solid.

EXAMPLES 35 to 37

According to the same method as in Example 34, the desired compounds (I") shown in Table 2 were obtained.

TABLE 2

$$\begin{array}{c} R^4 \\ \diagdown \\ C-COOR^{3"} \\ \diagup \\ CH_3-N \\ \diagdown \\ CO-N \end{array} \begin{array}{c} (I") \\ \diagup = N \\ \diagdown \end{array}$$

| Example | $R^4$ | $R^{3"}$ | Physical property |
|---|---|---|---|
| 34 | $CH_3$ | $-CH_2-\phantom{}\bigcirc\phantom{}-O-C_5H_{11}$ | m.p. 63~65° C. |
| 35 | " | $-CH_2-\phantom{}\bigcirc\phantom{}-O-C_6H_{13}$ | m.p. 60~62° C. |
| 36 | " | $-(CH_2)_4CH=CH_2$ | $n_D^{27}$ 1.4825 |
| 37 | " | $-C_4H_9-\phantom{}\bigcirc\phantom{}$ | $n_D^{27}$ 1.5272 |

EXAMPLE 38

Preparation of wettable agent

The compound of Example 1 (10.00 parts), 69.75 parts of kaolin, 18.00 parts of white carbon, 1.80 parts of Neopelex (trade name) and 0.45 part of Demol EP (trade name, produced by Kao Atlas) were uniformly mixed and pulverized to obtain a fine powdery wettable agent.

When this is to be used as the stalk and leaf spraying agent, it is diluted with water to 200- to 2000-fold before spraying on plants. When used as the seed disinfecting agent, it is diluted to 20- to 1000-fold and seeds or unhulled rice are dipped in the dilution for 10 minutes to 48 hours.

EXAMPLE 39

Preparation of emulsion

The compound of Example 1 (60 parts), 23 parts of methyl ethyl ketone and 17 parts of polyoxyethylene nonylphenyl ether were mixed and dissolved to obtain an emulsion.

When this is to be used as the stalk and leaf spraying agent, it is diluted with water to 500- to 4000-fold before spraying on plants. When used as the seed disinfecting agent, it may be diluted to 10- to 4000-fold and seeds or unhulled rice are dipped in the dilution for 10 minutes to 48 hours, or alternatively it may be powder coated as such at a ratio of 0.5 to 1 % by weight of the weeds or unhulled rice.

EXAMPLE 40

Preparation of powder

The compound of Example 23 (2 parts) and 98 parts of a clay were uniformly mixed and pulverized to obtain powder.

EXAMPLE 41

Preparation of granules

After 5 parts of the compound of Example 27, 25 parts of bentonite and 67 parts of white carbon were kneaded with addition of 15 parts of water, the kneaded product was granulated and dried by a fluidized dryer to obtain granules.

EXAMPLE 42

Activity test against rice "Bakanae" disease

Unhulled rice infected with rice "Bakanae" disease microorganism obtained by spray inoculation of a concentrated suspension of spores of rice "Bakanae" disease at flower blooming stage of rice (species: Nipponbare) was provided as a sample.

Disinfection of seeds was carried out by preparing a dilution to a predetermined concentration by use of the wettable agent prepared according to Example 38, and dipping the above sample unhulled rice at a chemical solution ratio (V/V) of 1:1 at 20° C. for 24 hours.

The sample unhulled rice after disinfection was dipped in water at 20° C. for 3 days, induced to germ at 30° C. over 24 hours, and when the germ became shaped like pigeon breast, it was seeded in cultivation soil according to the seedling box seedling growth method. Then, cultivation was managed in a glass greenhouse.

Disease outbreak was examined by withdrawing all the seedlings in the respective treated groups after 25 days after seeding (4-leaf stage), examining the number of rice "Bakanae" disease seedlings to determine the disease onset seedling ratio (%), and calculating the seed disinfection ratio (%) therefrom (repeated for 5 times for one group).

Also, chemical damage to rice was examined according to the same standard as in the foregoing test example, and evaluated according to 6 ranks (0: none, 1: slight, 2: some, 3: much, 4: excessive, 5: extremely excessive).

The results are as shown in Table 3 (the compound (I) used was shown by the number of Example in the column of Compound in the Table).

$$\text{Infected seedling ratio (\%)} = \frac{\text{Number of infected seedling}}{\text{Number of examined seedling}} \times 100$$

$$\text{Seed disinfection ratio (\%)} = \left(1 - \frac{\text{Infected seedling ratio of treated group}}{\text{Infected seedling ratio of non-treated group}}\right) \times 100$$

TABLE 3

| Compound (Example No.) | Concentration (ppm) | Seed disinfection ratio (%) | Chemical damage |
|---|---|---|---|
| 1 | 200 | 100 | 0 |
| 8 | 200 | 100 | 0 |
| 12 | 200 | 100 | 0 |
| 25 | 200 | 100 | 0 |
| 27 | 200 | 100 | 0 |
| 34 | 200 | 100 | 0 |
| 35 | 200 | 100 | 0 |
| 36 | 200 | 100 | 0 |
| 37 | 200 | 100 | 0 |
| Comparative chemical Benomil | 1000 | 98 | 0 |
| Compound A | 200 | 10 | 0 |
| Non-treated group | — | 0 | — |

•Benomil (commercially available agent)

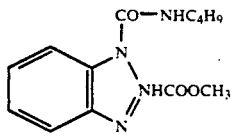

•Compound A (compound of Japanese Provisional Patent Publication No. 150590/1983)

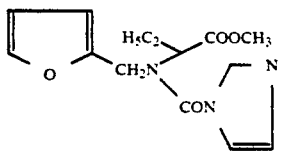

EXAMPLE 43

Control activity test against rice blast

By use of a plastic pot of 5 cm in diameter, at the 1.5-leaf stage of rice (species: Nipponbare) cultivated in soil in a greenhouse, each 10 ml of diluted solutions to predetermined concentrations of the wettable agent prepared according to Example 38 was sprayed thereon, and one day after, a suspension of rice blast microorganism spores was inoculated by spraying. After 5 days after inoculation, the number of lesions was examined.

The chemical agent effect was shown according to 6 ranks of 5 to 0, and one without lesion (i.e., 100% seed disinfection ratio) shown by 5, 10% or less of lesion area as compared with non-treated group by 4, about 20% by 3, about 40% by 2, about 60% by 1, and one wholly infected by 0. Also, chemical damage to rice was examined according to the same standards as in the foregoing test example, and evaluated according to the method of 6 ranks of Example 8.

The results are shown in Table 4.

TABLE 4

| Compound (Example No.) | Concentration (ppm) | Seed disinfection ratio (%) | Chemical damage |
|---|---|---|---|
| 1 | 200 | 100 | 0 |
| 5 | 200 | 100 | 0 |
| 8 | 200 | 100 | 0 |
| 9 | 200 | 100 | 0 |
| 12 | 200 | 100 | 0 |
| 23 | 200 | 100 | 0 |
| 25 | 200 | 100 | 0 |
| 27 | 200 | 100 | 0 |
| 34 | 200 | 100 | 0 |
| 35 | 200 | 100 | 0 |
| 36 | 200 | 100 | 0 |
| 37 | 200 | 100 | 0 |
| Comparative chemical EDDP | 200 | 4 | 0 |
| Compound B | 200 | 2 | 0 |
| Non-treated group | — | 0 | — |

•EDDP (commercially available agent)

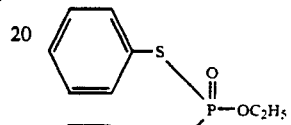

•Compound B (compound of Japanese Provisional Patent Publication No. 260572/1985)

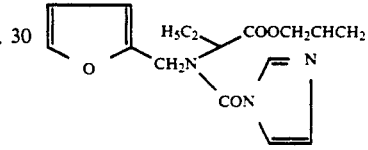

We claim:
1. An imidazole compound of the formula:

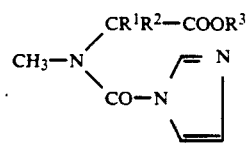

wherein $R^1$ and $R^2$ each represents a hydrogen atom or an alkyl group having 1 to 4 carbon atoms, provided that both of $R^1$ and $R^2$ do not represent an alkyl group at the same time, or together form a group $=CHR^4$, where $R^4$ represents an alkyl group having 1 to 4 carbon atoms; when $R^1$ and $R^2$ each represents a hydrogen atom or an alkyl group having 1 to 4 carbon atoms, $R^3$ represents an alkyl group having 1 to 12 carbon atoms, an alkenyl group having 1 to 12 carbon atoms, a phenyl-$C_{1-12}$-alkyl group, a phenyl-$C_{3-12}$-alkenyl group, a phenoxy-$C_{2-12}$-alkyl group or a phenoxy-$C_{3-12}$-alkenyl group, and the phenyl rings of the phenyl-$C_{1-12}$-alkyl, phenyl-$C_{3-12}$-alkenyl, phenoxy-$C_{2-12}$-alkyl and phenoxy-$C_{3-12}$-alkenyl groups are optionally substituted with at least one substituent selected from a halogen atom, a $C_{1-12}$-alkyl group, a $C_{1-12}$-alkoxy group, a $C_{3-12}$-alkenyloxy group and a phenoxy group; and when $R^1$ and $R^2$ together form the group $=CHR^4$, $R^3$ represents an alkyl group having 4 to 10 carbon atoms, an alkenyl group having 4 to 10 carbon atoms or a phenyl-$C_{1-12}$-alkyl group having a phenyl ring optionally substituted with at least one substituent selected from a halogen atom, a $C_{1-12}$-alkyl group, a $C_{1-12}$- alkoxy group, a $C_{3-12}$-alkenyloxy group and a phenoxy group.

2. The imidazole compound according to claim 1, wherein $R_1$ is a hydrogen atom or an alkyl group having 1 to 4 carbon atoms, $R^2$ is a hydrogen atom and $R^3$ is an alkyl group having 4 to 10 carbon atoms, a phenylalkyl group containing a straight $C_{1-5}$ alkyl group, a phenylalkenyl group containing a straight $C_{3-6}$ alkenyl group, a phenoxylalkyl group containing a straight or branched $C_{2-5}$ alkyl group or a phenoxyalkenyl group containing a straight or branched $C_{3-5}$ alkenyl group.

3. The imidazole compound according to claim 1, wherein $R^1$ is a hydrogen atom, a methyl group, an ethyl group or a propyl group and $R^3$ is an n-pentyl group, an n-hexyl group, an n-octyl group, an n-decyl group, an n-hexenyl group, an unsubstituted benzyl group, or a benzyl group substituted with at least one substituent selected from a halogen atom, a $C_{1-12}$-alkyl group, a $C_{1-12}$-alkoxy group, a $C_{3-12}$-alkenyloxy group and a phenoxy group.

4. The imidazole compound according to claim 1, wherein $R^1$ and $R^2$ together form the group $=CHR^4$, and $R^3$ is a straight or branched alkyl group having 4 to 10 carbon atoms, a straight or branched alkenyl group having 4 to 10 carbon atoms, or a phenyl-$C_{1-12}$-alkyl group substituted with a straight or branched alkyl group having 1 to 12 carbon atoms.

5. The imidazole compound according to claim 4, wherein $R^4$ is a methyl group and $R^3$ is a straight alkenyl group having 4 to 10 carbon atoms or a phenyl-$C_{1-12}$-alkyl group substituted with a straight alkyl group having 1 to 4 carbon atoms.

6. A fungicide composition comprising a fungicidally effective amount of a compound of the formula (I):

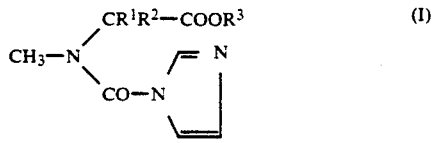

wherein $R^1$ and $R^2$ each represents a hydrogen atom or an alkyl group having 1 to 4 carbon atoms, provided that both of $R^1$ and $R^2$ do not represent an alkyl group at the same time, or together form a group $=CHR^4$, where $R^4$ represents an alkyl group having 1 to 4 carbon atoms;

when $R^1$ and $R^2$ each represents a hydrogen atom or an alkyl group having 1 to 4 carbon atoms, $R^3$ represents an alkyl group having 1 to 12 carbon atoms, an alkenyl group having 1 to 12 carbon atoms, a phenyl-$C_{1-12}$-alkyl group, a phenyl-$C_{3-12}$-alkenyl group, a phenoxy-$C_{2-12}$-alkyl group or a phenoxy-$C_{3-12}$-alkenyl group, and the phenyl rings of the phenyl-$C_{1-12}$-alkyl, phenyl-$C_{3-12}$-alkenyl, phenoxy-$C_{2-12}$-alkyl and phenoxy-$C_{3-12}$-alkenyl groups are optionally substituted with at least one substituent selected from a halogen atom, a $C_{1-12}$-alkyl group, a $C_{1-12}$-alkoxy group, a $C_{3-12}$-alkenyloxy group and a phenoxy group; and when $R^1$ and $R^2$ together form the group $=CHR^4$, $R^3$ represents an alkyl group having 4 to 10 carbon atoms, an alkenyl group having 4 to 10 carbon atoms or a phenyl-$C_{1-12}$-alkyl group having a phenyl ring optionally substituted with at least one substituent selected from a halogen atom, a $C_{1-12}$-alkyl group, a $C_{1-12}$-alkoxy group, a $C_{3-12}$-alkenyloxy group and a phenoxy group; according to claim 1 as the active ingredient, and a fungicidally acceptable carrier.

7. The fungicide composition according to claim 6, wherein $R^1$ is a hydrogen atom or an alkyl group having 1 to 4 carbon atoms, $R^2$ is a hydrogen atom and $R^3$ is an alkyl group having 5 to 10 carbon atoms, a straight alkenyl group having 4 to 10 carbon atoms, a phenylalkyl group containing a straight $C_{1-5}$ alkyl group, a phenylalkenyl group containing a straight $C_{3-6}$ alkenyl group, a phenoxylalkyl group containing a straight or branched $C_{2-5}$ alkyl group or a phenoxylalkenyl group containing a straight or branched $C_{3-5}$ alkenyl group.

8. The fungicide composition according to claim 6, wherein $R^1$ is a hydrogen atom, a methyl group, an ethyl group or a propyl group and $R^3$ is an p-pentyl group, an n-hexyl group, an n-octyl group, an n-decyl group, an n-hexenyl group, an unsubstituted benzyl group, or a benzyl group substituted with at least one substituent selected from a halogen atom, a $C_{1-12}$-alkyl group, a $C_{1-12}$-alkoxy group, a $C_{3-12}$-alkenyloxy group and a phenoxy group.

9. The fungicide composition according to claim 6, wherein $R^1$ and $R^2$ together form the group $=CHR^4$, and $R^3$ is a straight or branched alkyl group having 4 to 10 carbon atoms, a straight or branched alkenyl group having 4 to 10 carbon atoms, or a phenyl-$C_{1-12}$-alkyl group substituted with a straight or branched alkyl group having 1 to 12 carbon atoms.

10. The fungicide composition according to claim 9, wherein $R^4$ is a methyl group and $R^3$ is a straight alkenyl group having 4 to 10 carbon atoms or a phenyl-$C_{1-12}$-alkyl group substituted with a straight alkyl group having 1 to 4 carbon atoms.

* * * * *

UNITED STATES PATENT AND TRADEMARK OFFICE
CERTIFICATE OF CORRECTION

PATENT NO. : 5,110,827

DATED : May 5, 1992

INVENTOR(S) : Hisao SUGIURA ET AL.

It is certified that error appears in the above-identified patent and that said Letters Patent is hereby corrected as shown below:

Title page, insert as Assignee --Ube Industries, Ltd., Yamaguchi, Japan--.

Claim 2, column 13, line 4, change "$R_1$" to --$R^1$--; and column 13, line 6, after "having" insert --5 to 10 carbon atoms, a straight alkenyl group having--.

Claim 8, column 14, line 32, change "p-pentyl" to --n-pentyl--.

Signed and Sealed this

Twenty-first Day of September, 1993

*Attest:*

BRUCE LEHMAN

*Attesting Officer*  *Commissioner of Patents and Trademarks*